United States Patent [19]

Williams, III

[11] 4,017,511

[45] Apr. 12, 1977

[54] PREPARATION OF AROMATIC BISIMIDES

[75] Inventor: Frank J. Williams, III, Scotia, N.Y.

[73] Assignee: General Electric Company, Schenectady, N.Y.

[22] Filed: Mar. 24, 1976

[21] Appl. No.: 670,047

[52] U.S. Cl. .................... 260/326 N; 260/47 CP; 260/326 S

[51] Int. Cl.² .................................. C07D 209/34

[58] Field of Search ........ 260/326 N, 47 CP, 326 S

[56] References Cited

UNITED STATES PATENTS

| | | | |
|---|---|---|---|
| 3,847,867 | 11/1974 | Heath et al. | 260/47 CP |
| 3,879,428 | 4/1975 | Heath et al. | 260/326 N |
| 3,922,284 | 11/1975 | Heath et al. | 260/326 N |

*Primary Examiner*—Dolph H. Torrence
*Attorney, Agent, or Firm*—Joseph T. Cohen; Jerome C. Squillaro

[57] ABSTRACT

Aromatic bisimides can be prepared by effecting reaction between a 3- or 4-nitro-N-substituted phthalimide with an aromatic dihydroxy compound in the presence of a solid alkali-metal hydroxide and using a certain class of dipolar aprotic compounds, e.g., dimethyl formamide, as a solvent.

12 Claims, No Drawings

PREPARATION OF AROMATIC BISIMIDES

PREPARATION OF AROMATIC BISIMIDES

This invention relates to the preparation of aromatic bisimides by the process of effecting reaction between a 3- or 4-nitro-N-substituted phthalimide with an aromatic dihydroxy compound in the presence of a solid alkali-metal hydroxide and using a certain class of dipolar aprotic compounds as a solvent.

More particularly, the invention is concerned with a process for making aromatic bisimides of the general formula

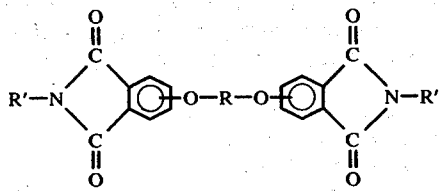

I which process comprises effecting reaction in the presence of a solid alkali-metal hydroxide between a nitro-N-substituted phthalimide of the general formula

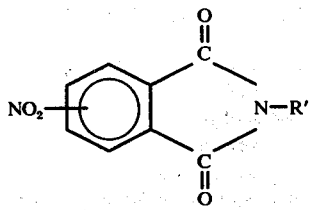

II with an aromatic dihydroxy compound of the general formula

     III

HO — R — OH where R is a member selected from the class consisting of (a) divalent radicals of the formula

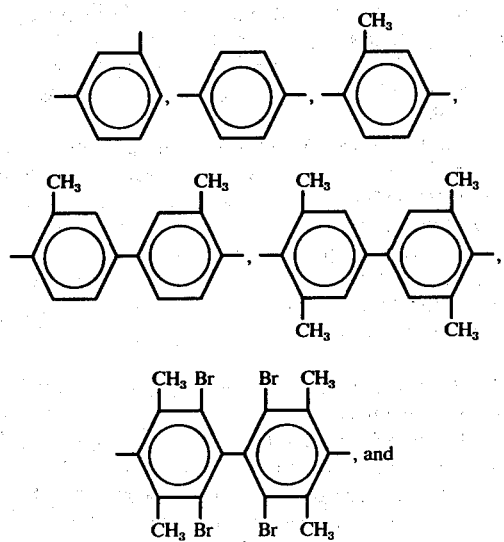

and (b) divalent organic radicals of the general formula

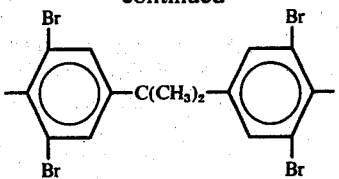

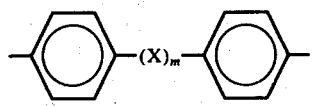

where X is a member selected from the class consisting of divalent radicals of the formulas $-C_yH_{2y}$,

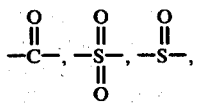

—O—, and —S—, where $m$ is 0 or 1, $y$ is a whole member from 1 to 5, and R' is the phenyl radical or an alkyl radical of from 1 to 2 carbon atoms, the said reaction being conduted in a dipolar aprotic solvent selected from the class consisting of N,N-dimethyl acetamide, dimethyl formamide (DMF), N-methyl pyrrolidone, and mixtures of such solvents. Dianhydrides of the general formula

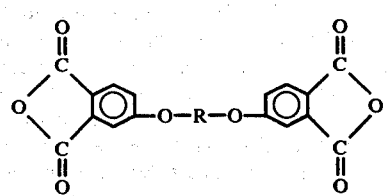

IV where R is the meanings given above have been used in the preparation of polymeric compositions by reacting the aforesaid dianhydrides with various organic diamines in the manner described in U.S. Pat. No. 3,847,867, issued Nov. 12, 1974, and assigned to the same assignee as the present invention which patent by reference is made part of the disclosures and teachings of the instant application. One of the important objectives in making these resins is to insure that the reactants required for such polymeric compositions are made as economically as possible in order that the ultimate cost of the resinous compositions will also be the lowest possible cost.

Several methods have been employed in the past for making the aforesaid aromatic bisimides of formula I. One method for making these aromatic bisimides comprises reacting a nitrophthalimide of formula II, with a dialkalimetal salt (dianion) of a dihydroxy aromatic compound, such as bisphenol-A [(2,2-bis-4-hydroxyphenyl)propane] to form the derivative of formula I. Thereafter, this bisimide can be treated with aqueous sodium hydroxide in water to form the corresponding tetracarboxylic acid and by suitable treatment of the tetracid with, for instance, glacial acetic acid and acetic anhydride, one can obtain the corresponding dianhydride of formula IV.

A more specific method for making the aforesaid bisimides of formula I comprises forming a mixture of the dihydroxy compound, for instance bisphenol-A, and sodium hydroxide in an aqueous medium with dimethyl sulfoxide (DMSO) and toluene. This mixture is heated to reflux to azeotropically remove water thereby producing an anhydrous dialkali metal salt. This salt is then reacted for a period of from 6 to 16 hours at about 60° C with the nitrophthalimide of formula II to give the crude aromatic bisimide. Thereafter the crude bisimide has to be washed several times with water, treated with, for instance, methanol several times to remove the impurities and the solid material is then washed again to obtain an aromatic bisimide of the desired purity, which can then be processed in a manner described above to form the dianhydride of formula IV, which in turn can be reacted with the organic diamine in the manner described in the aforesaid U.S. Pat. No. 3,847,867.

I have now discovered, unexpectedly that I am able to make the precursor aromatic bisimide of formula I more expeditiously and with fewer steps by effecting reaction, under substantially anhydrous conditions, between a nitrophthalimide of formula II with an aromatic dihydroxy compound of formula III by employing a substantially water-free alkali-metal hydroxide and a specific class of solvents. By means of my process, many of the steps and undesirable features of the previous method for making the bisimides of formula I were eliminated or obviated. Thus, whereas before dimethyl sulfoxide was necessary to help solubilize the dianion made from aqueous sodium hydroxide and the dihydroxy aromatic compound and thus make its drying more complete, (incomplete drying greatly affected the purity of the bisimide produced) the use of water is almost completely eliminated and strong unpleasant odors associated with the use of dimethyl sulfoxide (which was essential in the above-described process) are no longer a problem. Moreover, the refluxing with the aqueous base additionally made the use of dimethyl sulfoxide necessary, since most other dipolar aprotic solvents contained functionalities which reacted with the aqueous base. Furthermore, the dimethyl sulfoxide was difficult to recover since it could not be distilled at atmospheric pressure. Also, the necessity for azeotroping the formed water, which was time-consuming and expensive, before the addition of nitroimide is substantially eliminated. Finally, before reaction could take place with the nitrophthalimide, the dianion salt had to be cooled before adding the nitrophthalimide and then again heated for at least 6 hours to insure complete reaction.

By using my invention whereby a solid instead of an aqueous alkali-metal hydroxide is used with the dihydroxy aromatic compound and a dipolar aprotic solvent of a specific class is employed, the preparation of the bisimide proceeds readily with a minimum of steps and when isolated is of excellent purity being almost ready for use in the next step for hydrolysis and conversion to the dianhydride of formula IV.

Among the alkali-metal hydroxides which can be employed are, for instance, sodium hydroxide, potassium hydroxide, cesium hydroxide, and rubidium hydroxide. The sodium hydroxide is preferred since it gives good results and is less expensive than any of the other alkali-metal hydroxides. Preferably, the alkali-metal hydroxide should be as anhydrous as possible. Although in the case of some alkali-metal hydroxides completely anhydrous material may not be possible, generally any moisture which may be present should be that which is adsorbed on the alkali-metal hydroxide and for best results should not exceed 10–15% adsorbed moisture based on the weight of the alkali-metal hydroxide. The alkali-metal hydroxide can be in any form, such as pellets, powders, or as flakes, the important thing being that it is in a physical state which can permit ready reaction under the conditions of the above-described invention.

Among the nitrophthalimides which may be employed are for instance 3-, and 4-nitro-N-methylphthalimide, 3- and 4-nitro-N-ethylphthalimide, and 3- and 4-nitro-N-phenylphthalimide.

In addition to the aromatic dihydroxy compounds whih are obvious from a reading of formula III, other dihydric phenols which may be employed are, for instance, 2,2-bis-(2-hydroxyphenyl)propane;
2,4'-dihydroxydiphenylmethane;
bis-(2-hydroxyphenyl)-methane;
2,2-bis-(4-hydroxyphenyl)-propane    (hereinafter identified as "bisphenol-A" or "BPA")
1,1-bis-(4-hydroxyphenyl)-ethane;
1,1-bis-(4-hydroxyphenyl)-propane;
2,2-bis-(4-hydroxyphenyl)-pentane;
3,3-bis-(4-hydroxyphenyl)-pentane;
4,4'-dihydroxybiphenyl;
4,4'-dihydroxy-3,3',5,5'-tetramethylbiphenyl;
2,4-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide;
4,4'-dihydroxy diphenyl oxide; etc.

In carrying out the reaction, one should employ at least 2 mols of the phthalimide of formula II, and preferably from 2.1 to 4 or more mols of the latter per mol of the aromatic dihydroxy compound of formula III. Too large a molar excess of the phthalimide will present problems of separation and recovery of the unused nitrophthalimide.

The amount of alkali-metal hydroxide employed can be varied slowly. Generally, I have found that at least two mols of the alkali-metal hydroxide should be employed in connection with each mol of the dihydric phenol, and preferably from about 2.05 to 3 mols of the former per mol of the dihydric phenol are advantageously used. Molar equivalents above 3 may cause a drop in yield.

The amount of aprotic solvent used can also be varied widely but enough of the latter solvent should be used in order to form a liquid medium for effecting the reaction. On a weight basis, I have found it convenient to use from about 1 to 20 parts or more, by weight, of the selected aprotic solvent, per weight unit of the total weight of the two reactants, namely the nitrophthalimide of formula II and the dihydric phenol of formula III.

I have found that although the above-described class of aprotic solvent can be employed alone in the practice of the invention, additional improvement may be obtained if another inert solvent is employed with the aprotic solvent. Generally the solvent used will assist in obtaining a high enough boiling point (about 100° to 200° C) whereby refluxing of the reactants in the presence of the alkali-metal hydroxide can be effected. The cosolvent used with the aprotic solvent is any solvent which is inert to the reactants or to the resulting reaction mixture and should boil above 100° C. Among such cosolvents may be mentioned the isomeric xylenes, such as, m, o-, and p-xylene, toluene, chlorobenzene, bromobenzene, o-dichlorobenzene, anisole, ethylbenzene, mesitylene, octane, cycloheptane, diethyl and dimethyl ethers of ethylene glycol, etc. The inert cosolvent used should be generally liquid at room temperature, although this is not especially essential since it can also be a low melting solid which at reflux conditions or in the reaction mixture with the aprotic solvent forms a homogeneous solution. The cosolvent has an additional function of insolubilizing the alkali-metal nitrite formed in the reaction and effectively removes the danger of the latter attacking the phthalimide ring and thus reducing the yield of desired bisimide of formula I.

The temperature at which reaction is carried out in the practice of my invention may be varied fairly widely. Generally I have found that temperatures from 100° to 200° C are advantageously used. If lower temperatures are employed, the reaction goes at a slower pace, while if temperatures above 200° C are employed one is apt to find that damaging side reactions may be going on causing a reduction in the yield of the desired bisimide.

The time of reaction may also be varied widely and only those times should be used which give optimum yields with a minimum of side reactions or loss of reactants or product. Generally I have found that the reaction goes to substantial completion within a period of from one to ten hours or more.

When a cosolvent is used with aprotic solvent, the amount of inert cosolvent can be varied widely. Generally I have found that, just as in the case of using the aprotic solvent, the mixture of cosolvents should constitute on a weight basis of from 1 to 20 parts, or more of the total cosolvents per part of the reactants used. On a volume basis, the aprotic solvent and the inert cosolvent can vary quite widely, and can vary from about 10 to 90% of each of the solvents based on the total volume of the two solvents.

In all instances, substantially anhydrous conditions should be employed, and for best results an inert atmosphere should be employed such as conducting the reaction under a blanket of nitrogen. Stirring should be resorted to at all times in order to insure intimate contact of all the reactants and reagents required for optimum processing.

After the reaction is completed, the mixture can be diluted with methylene chloride which is a solvent for extracting the bisimide, and the methylene chloride solution can be washed several times with water and with an HCl solution of about 1 to 1.2 N HCl. The organic phase which will separate out is dried, for instance, with magnesium sulfate and concentrated by various means, such as under vacuum, to give a solid bisimide which is essentially pure at this stage. Thereafter, the bisimide can be processed in the manner described previously to make the aforementioned dianhydrides.

In addition to the advantages recited previously, my process offers several additional advantages over previous methods for making the bisimide from the reaction of a dihydric phenol and a nitrophthalimide employing an alkali-metal hydroxide in the form of the dianion of the dihydric phenol. In the past, the dianion salt formed from the reaction of the dihydric phenol and the alkali-metal hydroxide had to be kept under an inert atmosphere to avoid rapid air-oxidation and had to be completely anhydrous before it could be allowed to undergo the aromatic nitro-displacement reaction to form the bisimide compound. This required a long period of time, for instance, from three to four days using a complex step of azeotropic distillation with toluene. Even after most of the water had been removed, it was necessary to scavenge the remaining amounts of water with dehydrating agents. Furthermore, once the dianion salt had been dried, two equivalents of the nitrophthalimide were added and the displacement reaction was then allowed to proceed for another period of time ranging from about 6 to 24 hours with ultimate additional workup required of the reaction product to isolate the desired bis-imide.

My nitro-displacement reaction is significantly simplified because I am able to generate substituted-phenoxide ions in situ with the alkali-metal hydroxide in the presence of the nitrophthalimide, thus avoiding the need to prepare the dianion of the dihydric aromatic compound in advance. Although it was expected that imidering opening by the alkali-metal hydroxide would complete with the nitro-displacement reaction, it was surprising to find that if the ring-opened compound was formed, it can apparently ring-close again under these conditions to regenerate the nitro-imide which can undergo displacement. It was also unexpected to find that there was little reaction between the alkali-metal hydroxide and the dipolar aprotic solvents which contained amide functionalities. Thus, all the ingredients can be placed in the reaction pot at the same time, which simplifies the procedure and eliminates the later addition of nitro-imide.

In order that those skilled in the art may better understand how the present invention may be practiced, the following examples are given by way of illustration and not by way of limitation. All reactions were conducted under a nitrogen atmosphere were stirring.

EXAMPLE 1

A mixture of 4.74 grams (0.023 mol) of 4-nitro-N-methylphthalimide, 2.28 grams (0.01 mol) of BPA, 0.96 gram (0.024 mol) solid sodium hydroxide pellets, 30 ml anhydrous DMF, and 10 grams of 4A molecular sieves (to pick up moisture; any of the well-known molecular sieves used for the purpose can be employed) was heated under a nitrogen atmosphere for 9 hours at the reflux temperature of the mass (about 142° C.). After cooling to room temperature (about 25° C.), the mixture was diluted with 100 ml $CH_2Cl_2$, and filtered to remove the molecular sieves. The solution was washed twice with 100 ml water and twice with 100 ml of a 1.2N HCl solution to remove all traces of DMF. The organic phase was dried with magnesium sulfate and concentrated under vacuum to give 4.74 grams of a material which was shown by $^{13}C$ nmr to consist of 93% of the bisphenol-A bisimide (BPA-BI) of the formula

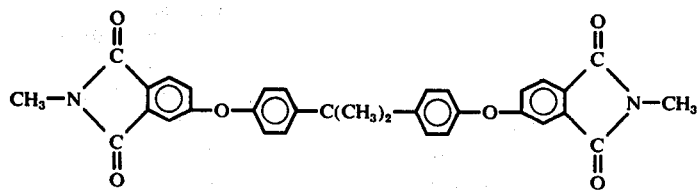

and 7% of the bisether

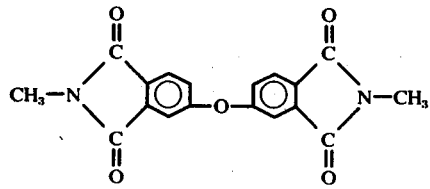

EXAMPLE 2

This example shows the advantage under equivalent conditions of using DMF over the previously used dimethylsulfoxide over and above the other disadvantages of using dimethylsulfoxide as the solvent for the reaction. More particularly, Example 1 was repeated except that the same amount of dimethylsulfoxide was substituted for the DMF. Upon working up the reaction mixture similarly as in Example 1, 4.36 grams of material was isolated, which was shown by $^{13}$C nmr to be a mixture of 73% of the BPA-BI of formula V, 3% of the bisether of formula VI, 5% of the half-displaced BPA-BI isomer of the formula

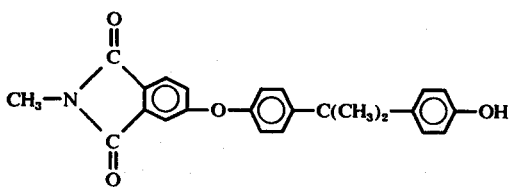

and 19% of the unreacted starting material 4-nitro-N-methylphthalimide. It is thus obvious that the use of the solid alkali-metal hydroxide with the DMF produced a materially greater yield of the desired BPA-BI than was possible by using the dimethylsulfoxide under comparable conditions.

EXAMPLE 3

In this example the conditions of reaction were repeated similarly as in Example 1 using 6.84 grams of BPA (0.03 mol), 13.59 grams 4-nitro-N-methylphthalimide (0.066 mol), 2.88 grams sodium hydroxide pellets (0.072 mol), 45 ml anhydrous DMF and 45 ml of o-xylene. The reaction mixture, however, was heated at 140° C. for 16 hours and worked up similarly as described in Example 1 to give 16.04 grams (98% yield) of BPA-BI which was essentially pure as shown by $^{13}$C nmr.

EXAMPLE 4

The conditions of the reaction were repeated similarly as in Example 1 with the exception that 4.64 grams of solid potassium hydroxide (containing about 13% water occluded therein) was substituted for the sodium hydroxide pellets used in Example 1. Upon working up the reaction mixture similarly as in Example 1, 18 grams of material were isolated which was shown by $^{13}$C nmr to consist of 61% of the BPA-BI, 33% of the half-displaced isomer, and 6% of the bisether of formula VI.

EXAMPLE 5

In this example a mixture of 6.84 grams BPA (0.03 mol), 12,66 grams 4-nitro-N-methylphthalimide (0.0615 mol), 2.52 grams of sodium hydroxide pellets (0.063 mol), 45 ml anhydrous DMF, and 45 ml o-xylene was stirred under a nitrogen atmosphere. The reactor was equipped with a recirculating Dean-Stark trap that contained 15.0 grams of activated 4A molecular sieves. The mixture of ingredients was placed in an oil bath maintained at a temperature of 170° C. and heated to the reflux temperature of the mass (internal temperature of the reaction mixture was about 142° C.). After 6 hours heating at the reflux temperature, the mixture was cooled to room temperature, diluted with 100 ml of methylene chloride, and the resulting homogeneous solution was washed twice with 100 ml water and twice with 100 ml of a 1.2N HCl solution. The organic phase was dried with magnesium sulfate and concentrated under vacuum to give 15.17 grams (93% yield) of a yellow solid which was shown by $^{13}$C nmr to be pure BPA-BI of formula V.

EXAMPLE 6

A mixture of 2.28 grams of BPA, 4.53 grams of 4-nitro-N-methylphthalimide, 0.96 g of sodium hydroxide pellets, and 30 ml of N,N-dimethyl acetamide was heated at 180° C. under a nitrogen atmosphere for 6 hours. Workup of the reaction mixture was again followed as described in the aforesaid Example 1 to give a material which was identified as the BPA bisimide of formula V in a yield of about 74%.

EXAMPLE 7

A mixture of 2.28 grams of BPA, 4.53 grams of 4-nitro-N-methylphthalimide, 0.96 gram of sodium hydroxide, and 30 ml of N-methylpyrrolidone was heated at 180° C. under a nitrogen atmosphere for 6 hours and the reaction mixture was worked up similarly as described in Example 1 to give the desired BPA-BI of formula V in about a 63% yield.

EXAMPLE 8

A mixture of 3.42 grams of BPA, 6.80 grams of 3-nitro-N-methylphthalimide, 1.44 grams of sodium hydroxide pellets, 11.5 ml anhydrous DMF, and 11.5 ml of o-xylene was treated exactly as described in Example 1. After 21 hours of reaction, the mixture was worked up similarly as in Example 1 to give 6.12 grams (75% yield) of material which was shown to be essentially pure aromatic bisimide when established by $^{13}$C nmr of the formula

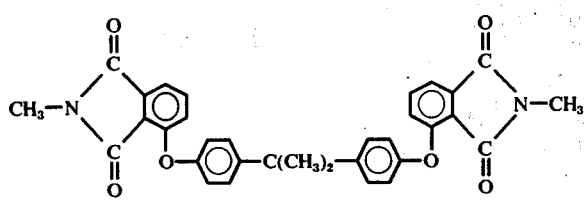

VII

EXAMPLE 9

A mixture of 13.68 grams of BPA, 24.68 grams of 4-nitro-N-methylphthalimide, 1.30 grams of 3-nitro-N-methylphthalimide 5.28 grams of sodium hydroxide pellets, 45 ml DMF and 45 ml of o-xylene was treated as described in the aforementioned Example 5. Workup and analysis of the reaction mixture by $^{13}C$ nmr after 21 hours of reflux heating indicated that the reaction was complete and that the resulting bisimide contained 90% of the 4,4'-isomer of formula V, and 10% of the 3,4'-isomer of the formula

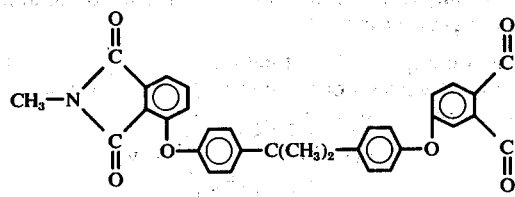

VIII

EXAMPLE 10

A mixture of 2.28 grams of BPA, 5.90 grams of 4-nitro-N-phenylphthalimide, 0.96 gram sodium hydroxide pellets, 15 ml of DMF, and 15 ml of o-xylene was treated in the same manner as described in Example 5. After 21.5 hours of reflux, the reaction mixture was worked up again similarly as in Example 1 to give an 85% yield of the desired aromatic bisimide which was shown to be pure by $^{13}C$ nmr and to have the formula

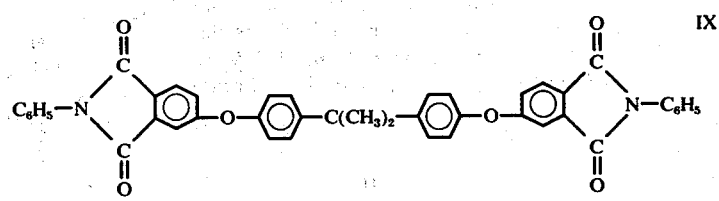

IX

EXAMPLE 11

A mixture of 25.98 grams 4-nitro-N-methylphthalimide, 5.28 grams sodium hydroxide pellets, 11.17 grams 4,4'-dihydroxybiphenyl, 45 ml DMF and 45 ml o-xylene was treated similarly as described in Example 1. After 21 hours of reaction, the mixture was worked up similarly as in Example 1 to give 29.75 grams (98% yield) of a bisimide whose structure as established by $^{13}C$ nmr was

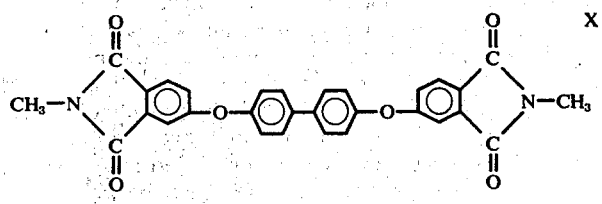

X

EXAMPLE 12

A mixture of 25.98 grams 4-nitro-N-methylphthalimide, 5.28 grams sodium hydroxide pellets, 13.10 grams 4,4'-dihydoxydiphenyl sulfide, 45 ml DMF and 45 ml o-xylene was treated similarly as in Example 1. After 21 hours of reaction the mixture was worked up as in Example 1 to give 29.48 grams (91.5% yield) of a bisimide whose structure, as confirmed by $^{13}C$ nmr, was

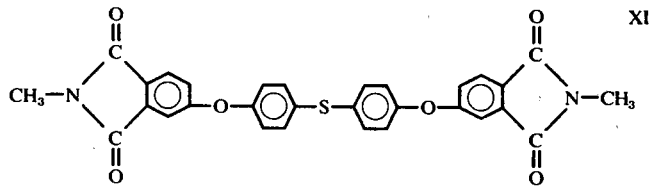

XI

EXAMPLE 13

A mixture of 5.35 grams 4-nitro-N-methylphthalimide, 1.09 grams sodium hydroxide pellets, 2.50 grams 4,4'-dihydroxydiphenyl oxide, 9.0 ml DMF and 9.0 ml o-xylene was treated and worked up similarly as described in Example 1 to give a bisimide in 89% yield (5.73 grams) of the formula (as confirmed by $^{13}C$ nmr)

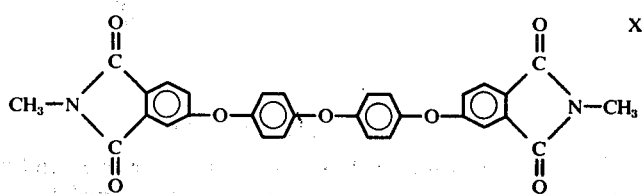

It will of course be apparent to those skilled in the art that instead of using the nitrophthalimides of the foregoing examples, other nitrophthalimides, examples of which have been given above, can be employed in their place without departing from the scope of the invention. In addition, instead of employing the alkali-metal hydroxides and the dihydric phenols recited in the previous examples, other alkali-metal hydroxides and dihydric phenols, many examples which have been recited previously, can be used in their place within the intended scope of the invention and with equivalent results. Finally, it will be apparent that the concentrations of ingredients and the conditions of reaction can also be varied widely as previously recited to obtain the desired aromatic bisimides expeditiously and usually in almost quantitative yields.

As pointed out above, the aromatic bisimides obtained in accordance with the present invention may be hydrolyzed to the tetraacids and then dehydrated to form the dianhydrides which in turn can be reacted with various organic diamines such as metaphenylene diamine, 4,4'-diaminodiphenylmethane, benzidine, 4,4'-diaminodiphenylsulfone, 3,3'-dimethylbenzidine, etc., to yield resinous compositions which because of their desirable heat resistance can be employed in applications where elevated temperatures may be encountered. Thus, these polymeric compositions, whether filled or unfilled, can be employed in applications requiring good mechanical, electrical and heat resistance properties. They are eminently suitable for use in the manufacture of insulators, transformer blocks, motor armatures, printed circuits, honeycomb structure panels and compressor vanes, etc. In the form of solutions with suitable solvents, they can be used to coat electrical conductors such as copper or aluminum wire and the resinous materials so deposited can be heat-treated to effect conversion to the final polymerized state.

What I claim as new and desire to secure by Letters Patent is:

1. The process for making aromatic imides of the general formula

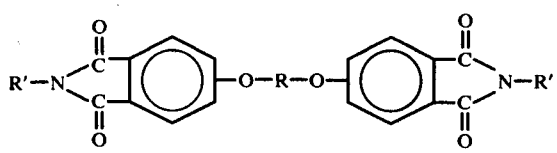

XII which comprises (1) effecting reaction under substantially anhydrous conditions between a nitrophthalimide of the general formula

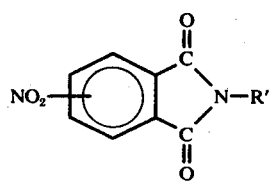

with a dihydroxy compound of the general formula

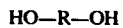

HO—R—OH where r is a member selected from the class consisting of a. divalent radicals of the formula

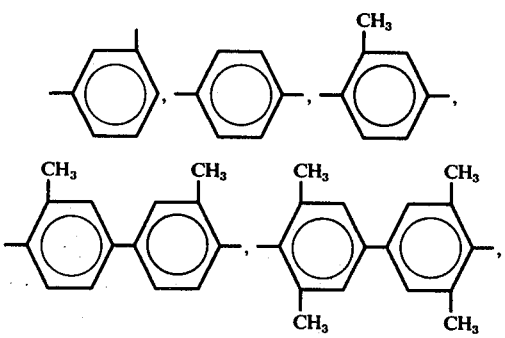

-continued

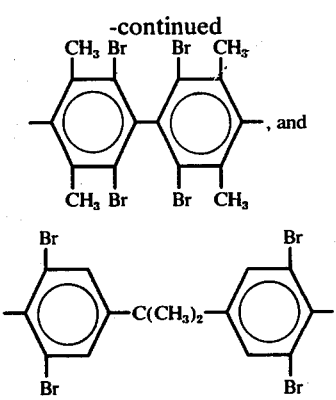

and
b. divalent organic radicals of the general formula

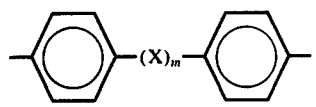

where X is a member selected from the class consisting of divalent radicals of the formulas —C$_y$H$_{2y}$,

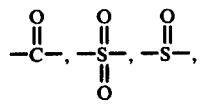

—O— and —S—, where $m$ is 0 or 1, $y$ is a whole number from 1 to 5, and R' is a phenyl radical or an alkyl radical of from 1 to 2 carbon atoms, the said reaction being conducted in a solvent selected from the class consisting of dimethyl formamide, dimethyl acetamide, N-methylpyrrolidone, and mixtures of such solvents and in the presence of a substantially water free solid alkali-metal hydroxide, and (2) isolating the formed aromatic bisimide.

2. The process as in claim 1 wherein the nitrophthalimide is 4-nitro-N-methylphthalimide.

3. The process as in claim 1 wherein the dihydroxy compound is bisphenol-A.

4. The process as in claim 1 wherein the alkali-metal hydroxide is sodium hydroxide.

5. The process as in claim 1 wherein the solvent is dimethyl formamide and xylene is used as a cosolvent.

6. The process as in claim 1 wherein the solvent is N,N-dimethyl acetamide.

7. The process as in claim 1 wherein the solvent is N-methylpyrrolidone.

8. The process as in claim 1 wherein from about 2.05 to 3 mols of the alkali-metal hydroxide are employed per mol of the dihydroxy compound.

9. The process as in claim 1 wherein the dihydroxy compound is 4,4'-dihydroxy diphenyl.

10. The process as in claim 1 wherein the dihydroxy compound is 4,4'-dihydroxy diphenyl oxide.

11. The process as in claim 1 wherein the dihydroxy compound is 4,4'-dihydroxy diphenyl sulfide.

12. The process for making a bisimide having the formula

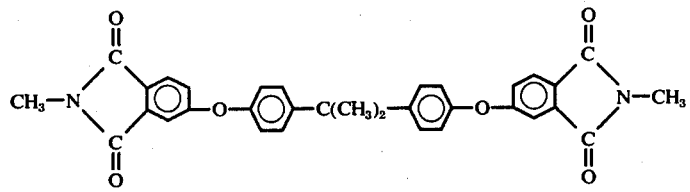

which comprises effecting reaction under substantially anhydrous conditions between 4-nitro-N-methylphthalimide and bisphenol-A in the presence of substantially water-free solid sodium hydroxide, dimethyl formamide as the solvent, and a cosolvent of xylene.

* * * * *